United States Patent [19]

Magers et al.

[11] 4,288,541

[45] Sep. 8, 1981

[54] ASCORBATE RESISTANT COMPOSITION, TEST DEVICE AND METHOD FOR DETECTING A COMPONENT IN A LIQUID TEST SAMPLE

[75] Inventors: Thomas A. Magers, South Bend, Ind.; John E. Sheats, Princeton, N.J.; David L. Tabb, Elkhart, Ind.

[73] Assignee: Miles Laboratories, Inc., Elkhart, Ind.

[21] Appl. No.: 84,611

[22] Filed: Oct. 15, 1979

[51] Int. Cl.³ .......................... C12Q 1/28; C12Q 1/54
[52] U.S. Cl. .................................... 435/14; 23/230 B; 23/901; 23/932; 252/408; 435/4; 435/28; 435/805; 435/810
[58] Field of Search ...................... 23/230 B, 932, 901; 252/408 R; 260/431; 424/2, 7; 435/4, 11, 14, 25, 26, 28, 805, 810

[56] References Cited

U.S. PATENT DOCUMENTS

| | | |
|---|---|---|
| 3,266,868 | 8/1966 | Harvill .................................. 435/14 |
| 3,367,842 | 2/1968 | Rupe et al. ............................ 435/14 |
| 3,411,887 | 11/1968 | Ku ...................................... 23/230 B |

FOREIGN PATENT DOCUMENTS

| | | | |
|---|---|---|---|
| 2215140 | 10/1974 | France .................................... 424/7 |
| 1444294 | 7/1976 | United Kingdom .................... 424/7 |

*Primary Examiner*—Peter A. Hruskoci
*Attorney, Agent, or Firm*—Edward H. Gorman, Jr.

[57] ABSTRACT

A composition, device and method for determining the presence of a component in a test sample which contains an interfering substance, such as ascorbic acid, are disclosed. The composition comprises an oxidase or other substance capable of producing peroxide in the presence of the component, a peroxidatively active substance, a chromogen capable of providing a detectable response (such as a color change) in the presence of peroxide and a peroxidatively active substance, and a complex of mercuric ion and one or more ligands wherein (a) the ligand binds covalently to the ion to form a water-soluble complex, and the ligand is not oxidizable by the complexed ion, and (b) the complex has a stability constant, $K_s$, of at least $10^7$ and is substantially noninterfering with respect to the detectable response.

18 Claims, No Drawings

ASCORBATE RESISTANT COMPOSITION, TEST DEVICE AND METHOD FOR DETECTING A COMPONENT IN A LIQUID TEST SAMPLE

BACKGROUND OF THE INVENTION

1. Field of the Invention

The present invention relates to minimizing the interfering effects of certain reducing agents on the analysis of a component in a liquid test solution containing one or more of these interfering substances.

The art of analytical chemistry has been greatly advanced since biochemistry began emerging as a primary scientific frontier requiring increasingly sophisticated analytical methods and tools to solve problems, the solutions of which were never before attempted. Likewise, the medical profession has lent impetus to the growth of analytical chemistry, requiring both high precision and speed in obtaining results. This remarkable progress has been still further spurred by industries such as brewing, chemical manufacturing, and others.

To satisfy the needs of these expanding technologies, a myriad of analytical procedures, compositions and apparatuses have evolved, including solution chemistry techniques, automated machinery and the so-called "dip-and-read" reagent strips. It is to the last of these that the present invention is primarily directed, although substantial benefit ultimately inures to the other procedures as well.

Reagent strip type test devices enjoy wide use in many analytical applications, especially in the chemical analysis of biological fluids, because of their relative low cost, ease of utilizability and speed in obtaining results. In medicine, for example, numerous physiological functions can be monitored merely by dipping reagent strips into a sample of body fluid, such as urine, and observing a detectable response such as a change in color or a change in the amount of light reflected from or absorbed by the strip.

Compatible with such "dip-and-read" methods have arisen many chemistries for detecting body fluid components. Most of these produce a detectable response which is quantitative or at least semi-quantitative. Thus, by measuring the response after a predetermined time, the analyst can obtain not only a positive indication of the presence of a particular constituent in a test sample, but also an estimate of how much of the constituent is present. Such strips provide the physician with a facile diagnostic tool as well as the ability to gauge the extent of disease or bodily malfunction.

Illustrative of dip-and-read strips currently in use are products available from the Ames Division of Miles Laboratories, Inc. under the trademarks CLINISTIX®, MULTISTIX®, KETOSTIX®, N-MULTISTIX®-C, DIASTIX®, DEXTROSTIX®, and others. Test devices such as these usually comprise one or more carrier matrices, such as absorbent paper, having respectively incorporated with them a particular reactant system which manifests a color change in the presence of a specific test sample components. Depending on the reactant system incorporated with a particular matrix, these devices can detect the presence of glucose, ketone bodies, bilirubin, occult blood, nitrite, and other pathological substances. The specific color change and the intensity of the color observable within a specific time range after contacting the strip with the sample is indicative of the presence of a particular component and its concentration in the sample. Some of these test devices and their reactant systems are set forth in U.S. Pat. Nos. 3,123,443 (CLINISTIX®); 3,212,855 and 4,147,514 (KETOSTIX®); 3,814,668, 3,164,534 and 2,981,606 (DIASTIX®); and 3,298,789, 3,092,465, 3,164,534 and 2,981,606 (DEXTROSTIX®).

2. Description of the Prior Art

The history of sugar analysis is perhaps most noteworthy because it has seen dramatic change over the years, both in the basic chemistries utilized and in its format. For the most part these analyses can be characterized as oxidizing systems which, when reduced, initiate reaction conditions leading to a detectable response, such as a color change or change in wavelength of ultraviolet light absorbed or reflected by the system. Thus, reducing sugars will convert silver oxide to metallic silver, and, if a solution of the sugar is applied to a piece of filter paper impregnated with silver oxide, a black dot develops. F. Feigl, *Chem. Ind.*, Vol. 57, p. 1161, London (1938). Similarly, o-dinitrobenzene and the 3,4-and 3,5-isomers of dinitrophthalic acid give a sensitive color reaction (forming violet shades) when heated with reducing sugars in $Na_2CO_3$. T. Momose, et al., *Chem. Pharm. Bull. Tokyo*, Vol. 12, p. 14 (1964); F. Feigl, *Spot Tests in Organic Analysis*, 7th Edition, pp. 338–339, Elsevier Publ. Co., New York (1966).

But as early as 1849 it was known that reducing sugars would cause an alkaline solution of $CuSO_4$ to precipitate the yellow to red Cooper(I)oxide (or oxyhydrate). H. Fehling, *Ann.*, Vol. 72 (1849). See also B. Herstein, *J. Am. Chem. Soc.*, Vol. 32, p. 779 (1910). This early milestone, known as the Fehling test, lent impetus to the development of a far more sensitive test which utilized silver oxide in ammonia, the so-called Tollens reagent, which reacts readily with reducing agents to produce a black precipitate of metallic silver, often forming a mirror on the inside walls of glass reaction vesssels. B. Tollens, *Ber.*, Vol. 14, p. 1950 (1881); Vol. 15, p. 1635, 1828 (1882).

Because of the relatively high incidence of *diabetes mellitus* and its accompanying serious clinical consequences, high interest from the biological and medical professions arose in new technique for analyzing glucose levels in urine and serum. This keen interest led to the development of several procedures which deviate dramatically from their solution chemistry forbears. These utilize sophisticated biochemical systems which can be incorporated into dry, dip-and-read devices, used in solutions or suspension techniques, or in conjunction with spectrophotometers and other hardware.

Of these new techniques, the present invention lends itself especially well to an enzymatic system wherein the analyte, for instance glucose, is a substrate for a particular enzyme, the reaction products being capable of eliciting a detectable response for chromogenic indicator compounds, such as those known loosely in the art as "benzidine-type indicators". These will be more carefully defined, infra, but for the present suffice it to say these compounds can undergo color changes in the presence of hydrogen peroxide and a peroxidative substance, such as the enzyme peroxidase. The glucose/glucose oxidase system exemplifies the prior art, wherein glucose is oxidized to gluconic acid with the concomitant formation of $H_2O_2$ in accordance with:

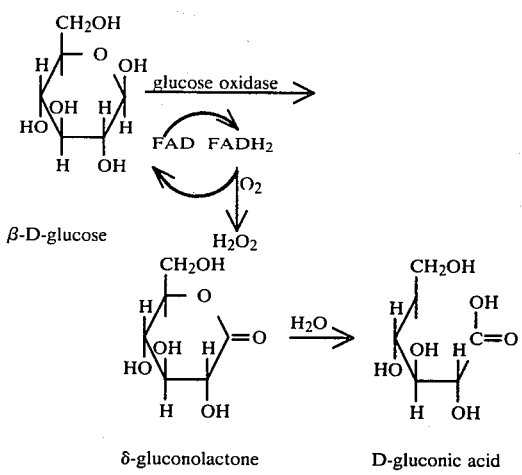

β-D-glucose

δ-gluconolactone    D-gluconic acid

It is the formation of hydrogen peroxide which facilitates the subsequent, indicator-related steps leading to observable color formation or other detectable response. Thus a benzidine-type indicator responds in the presence of hydrogen peroxide and peroxidase by changing its light absorptive capability.

In practice, this technology is presently utilized for glucose analysis in the form of dip-and-read reagent strips such as those marketed by the Ames Division of Miles Laboratories, Inc. under the trademark CLINISTIX® and others. Broadly, these comprise a plastic strip, at one end of which is mounted an absorbent paper portion impregnated with the appropriate enzymes, indicator compound and buffering agents as the principal active ingredients. They are used by dipping the reagent-bearing end into the test sample, removing it and comparing any color formed in the paper with a standard color chart calibrated to various glucose concentrations.

Despite the remarkable gains provided by the reagent strips, certain substances often present in the test sample are often found to interfere with the accuracy of the test. When the concentrations of such substances reach a certain threshold level, in comparison to that of the substrate measured, the adverse effect on the test can become marked. For example, those skilled in the art of reagent strips have for a long time been aware that the presence of ascorbic acid in urine can adversely affect the analysis of such nonrelated components as glucose, occult blood, bilirubin, and nitrite. Thus, high urinary concentration of ascorbic acid from therapeutic doses of vitamin C or parenteral preparations which contain vitamin C as a reducing agent; e.g., tetracyclines, can inhibit the reaction of such tests and limit their accuracy.

The prevalence of this long unvolved problem is indeed evidenced by the many attempts to surmount it recorded in the prior art. U.S. Pat. No. 3,411,887 to Ku, and assigned to the present assignee, discloses the use of a metal ion having an oxidation-reduction potential above that of the interfering substance, but below that of the chromogenic substance or indicator. While this approach appears theoretically feasible, and does somewhat minimize interference from ascorbic acid, it reduces the quantitative accuracy of the indicators in sugar-sensitive reagent systems, especially glucose systems. Primarily, the difficulty appears to stem from a severe lack of storage stability of a sugar-sensitive indicator composition in the presence of the metal ion.

Because of the reduced shelf life and lack of quantitative response, the compounds described in U.S. Pat. No. 3,411,887 have never performed sufficiently well to produce a reliable sugar test; the cure being worse than the malady.

U.S. Pat. Nos. 3,975,398 and 3,988,208 disclose indicator compounds purported to be uninhibited by acetoacetic acid or ascorbic acid. Other attempts at solving this problem of interference were through the use of ion-exchange substances (British Pat. No. 1,193,594) and multi-layered carrier matrices (British Pat. No. 1,171,788) in hopes that the interfering substances could be physically separated from the test sample prior to contacting the reagent system.

Despite long continued efforts such as those described above, to date no substantial solution to the problem has been devised. The "trapping system" of U.S. Pat. No. 3,411,887, as will be demonstrated by the Examples, infra, provides compositions of marginal stability. Test devices utilizing such technology are virtually useless after just a brief period of storage at room temperature.

The present invention solves this long-felt need for an indicator system having a substantial resistance to interference from reducing agents such as ascorbic acid (vitamin C).

SUMMARY OF THE INVENTION

Briefly stated, the present invention is based upon an improved composition capable of detecting the presence of a component in a liquid test sample. The prior art composition which applicants have improved comprises a reagent system capable of producing a detectable response, such as a color change, in the presence of the component, and a reducing agent trapping system comprising a compound of a heavy metal ion having an oxidation potential between that of the chromogenic substance and that of a reducing agent having an oxidation potential similar to that of ascorbic acid. This composition has been dramatically improved by applicants (and it is here wherein the present invention lies) by providing the metal ion as a complex of $Hg^{++}$ and a specific class of ligands. The ligand is bonded covalently with the mercuric ion to form a water-soluble complex, and it has a higher oxidation potential that the ion in its complexed state. The complex has a stability constant, $K_s$, greater than about $10^7$, and is substantially noninterfering with the reagent system.

The invention additionally comprises a test device made by incorporating the composition with a carrier matrix; as well as a method for analysis utilizing the composition or device by contacting either with the test sample and observing a detectable response.

DETAILED DESCRIPTION OF THE INVENTION

The use of the presently claimed mercuric ion/ligand complex (hereinafter "the complex") is indeed unique. Even when test solutions contain relatively high amounts of reducing agents, analysis is still possible, whereas accurate determination in such test samples was heretofore impossible without having first removed the interferant prior to analysis. For example, the complex of the present invention has been found to facilitate accurate analysis of glucose in urines containing up to 200 milligrams per deciliter (mg %) of ascorbic acid. Yet, such compositions are unexpectedly stable when compared with prior art compositions, none of which has even come close to such utility, while simultaneously providing a product stable enough to withstand storage over more than minimal periods.

After applicants' initial successful experiment with an amino acid complex with $Hg^{++}$, many additional amino acids were tried as ligands. Some worked; some did not. Moreover, it was later found that other compounds, seemingly chemically unrelated to amino acids, were equally effective as ligands in the complex. Again, some worked and some did not.

Because of this large diversity of ligands which provide both stable complexes with mercuric ion as well as abatement of interference from reducing agents, applicants have gone to considerable lengths to identify that thread of community of properties shared by all of the ligands and complexes found to be successful, and not shared by the unsuccessful candidates. This thread is believed to comprise the four parameters of (a) the ability of the ligand to bind substantially covalently to the mercuric ion, while yielding a water-soluble complex, thus leaving the ionic nature of the ion substantially free to interact with the interfering reducing agent, (b) a ligand oxidation potential higher than that of mercuric ion in the complexed state, so that the ion cannot promote oxidative decomposition of the ligand upon storage, (c) a stability constant for the complex of at least about $10^7$, so that the ligand and ion are not bound too loosely or tightly, thereby rendering the complex either too unstable to prevent $Hg^{++}$ hydrolysis, or too tightly bound so as to shield the metal ion from its environment to the extent that it can no longer interact with the interferant reducing agent, and (d) the inability of the complex or its reaction products after reduction to interfere with the reagent system.

Before proceeding with further discussion of the complexes, it is useful to explore certain theoretical aspects of the chemistry of mercuric ion and its ability to bind covalently with certain ligands. $Hg^{++}$ is considered a strong Lewis acid, behaving similarly to HF or $H_2PO_4^-$ in aqueous media, and it readily hydrolyzes to form hydroxy complexes in accordance with $$Hg^{++} + H_2O \rightleftharpoons HgOH^+ + H^+ \qquad (1)$$

The equilibrium constant for this reaction can be expressed as

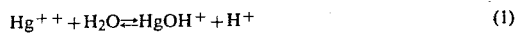

$$K = \frac{[HgOH^+][H^+]}{[Hg^{++}]} = 3.2 \times 10^{-3} \qquad (2)$$

Going one step further, $HgOH^+$ easily hyrolyzes to $Hg(OH)_2$, which disproportionates to form yellow HgO and water according to the overall reaction $$Hg^{++} + 2OH^- \rightleftharpoons Hg(OH)_2 \rightleftharpoons HgO + H_2O \qquad (3)$$

The solubility product for mercury(II)hydroxide in this reaction is $$K_{sp} = [Hg^{++}][OH^-]^2 = 4 \times 10^{-26} \qquad (4)$$

From the values for the equilibrium constants relating to the hydrolysis of $Hg^{++}$ (equations 2 and 4) it is evident that $Hg^{++}$ is stable in aqueous solution only at pH levels below about 2, absent stabilizing complexing agents. At slightly higher pH values the predominant species is $HgOH^+$, and at pH >3 HgO will precipitate almost quantitatively.

Small wonder that when the present applicants attempted to use the teachings of U.S. Pat. No. 3,411,887, mentioned supra, severe discoloration and loss of quantitation and storage capability resulted. Without some means of stabilizing $Hg^{++}$ on the shelf as well as in solution, a means provided by the present invention, the strongly colored HgO spontaneously forms after relatively brief storage periods, or upon use, rendering the test composition both sensitive to interfering reducing agents, and unreliable from both qualitative and quantitative standpoints. Thus, the present discovery is immersed in the truism that mercuric compounds in solutions above pH 3 are unstable unless hydrolysis is precluded, such as by complexing $Hg^{++}$ with some ligand capable of imparting sufficient stability. Applicants discovered not only complexing ligands which effect that required stabilization (as well as many which didn't), but also ligands which permit the complex to function excellently in removing reducing agent interference.

The first of the four criteria which applicants believe relates the presently claimed ligands to one another is the ability to bind covalently to $Hg^{++}$ while simultaneously providing water-soluble complexes. Among ligands which can bind to $Hg^{++}$ covalently are $CN^-$, $SCN^-$, $Cl^-$, $Br^-$, $I^-$, acetate, $NH_3$, $CH_3NH_2$, pyridine, aniline, ethylenediamine, ethylenediaminetetraacetic acid, triphenylphosphine, amino acids, carboxamides, imides, heterocyclic amides such as uridine, and many others. Accordingly, in exploring possible ligands to produce the complex, one begins by determining which ones will covalently bind with $Hg^{++}$. There are many.

Next, one inquires into whether a complex of the ligand will dissolve to an appreciable extent in water. A solubility sufficient to produce an aqueous concentration of at least about 0.01 M is presently considered adequate for the complex, although complexes capable of forming at least about 0.1 M solutions in water at standard pressure and temperature (STP) are preferable.

Given a list of ligands which bind covalently to $Hg^{++}$ to form water-soluble complexes, the next step is to explore which of those will not be oxidized by the metal ion. If the ligand has too low an oxidation potential relative to mercuric ion, the complex will be susceptible to decomposition, leading to its inability to eliminate reducing agent interference. One way of exploring ligand susceptibility to oxidation by complexed mercuric ion is to prepare a solution of the complex in water, and observe at STP for several days. The precipitation of grey, metallic mercury is indicative of an unacceptable ligand oxidation potential.

The third parameter to be explored in determining ligands whose mercuric complexes solve the problem of reducing agent interference is the thermodynamic criterion known as the stability constant ($K_s$). As was seen, supra, because of the spontaneous formation of yellow HgO from $Hg^{++}$ at pH's above about 3, and because of that ion's penchant for slowly forming HgO in the dry state, complexing ligands are needed. The stabilizing influence of various ligands can be assessed by $K_s$ data of the particular $Hg^{++}$/ligand complex. The formation of the complex is expressed as $$Hg^{++} + nL \rightleftharpoons HgL_n \qquad (5)$$

The $K_s$ for this reaction is expressed as $$K_s = \frac{[HgL_n]}{[Hg^{++}][L]^n} \quad (6)$$

In equations (5) and (6), L is a ligand, n is the number of such ligands bound to the metal ion, and $HgL_n$ is the complex. Common values for n are 2, 3 or 4, but can be as high as 6. It is to be understood that $HgL_n$ can be a heterogeneous complex wherein $L_n$ can comprise different ligands bound to the same ion.

From equation (4) we have $$[Hg^{++}] = \frac{4 \times 10^{-26}}{[OH]^2} \quad (7)$$

Substituting this relationship in equation (6), we obtain $$K_s = \frac{[OH^-]^2[HgL_n]}{4 \times 10^{-26}[L]^n} \quad (8)$$

For the purpose of determining numerical values for $K_s$, and therefore describing the complex in numerical terms, several conventions will be employed herein. Since relatively high, substantially equimolar concentrations of ligand L and complex $HgL_n$ are desirable in preparing the test devices of the present invention, and since such concentrations approach unit activity, it will be herein assumed that $$[HgL_n] \simeq [L]^n \simeq 1 \quad (9)$$

This assumption simplifies equation (8) to $$K_s = \frac{[OH^-]^2}{4 \times 10^{-26}} \quad (10)$$

Thus, it can be seen that $K_s$ plays an important role in defining complexes which will be stable at various pH conditions, according to equation (10). Table I shows how this mathematical relationship can be expressed in terms of the $K_s$ a complex needs in order to prevent its being converted to HgO at various pH's.

TABLE I

| $K_s$ Needed to Prevent HgO Formation | | |
|---|---|---|
| pH | [OH$^-$] | $K_s$ |
| 4 | $10^{-10}$ | $2.5 \times 10^5$ |
| 5 | $10^{-9}$ | $2.5 \times 10^7$ |
| 6 | $10^{-8}$ | $2.5 \times 10^9$ |
| 7 | $10^{-7}$ | $2.5 \times 10^{11}$ |
| 8 | $10^{-6}$ | $2.5 \times 10^{13}$ |
| 9 | $10^{-5}$ | $2.5 \times 10^{15}$ |
| 10 | $10^{-4}$ | $2.5 \times 10^{17}$ |
| 11 | $10^{-3}$ | $2.5 \times 10^{19}$ |

It can be seen from the Table that in order to keep a mercuric complex in solution at a pH of 6, i.e., in the pH range of normal urine, it should have a $K_s$ of $2.5 \times 10^9$. It has been found that complexes with a $K_s$ of as low as about $10^5$ are stable at a pH of about 4. While these values are not absolute, it has been found preferable that the complex have a $K_s$ of at least about $10^7$.

The last criteria to be satisfied by the complex of the present invention is that of noninterference with the reagent system and the latter's ability to detect the presence of the analyte. Clearly, a complex which reacts chemically with the system, or which inhibits an enzyme crucial to the quantitativeness of the response to the presence of the component, will defeat the purpose of the present invention. Moreover, the complex must not yield, upon its reduction by an interfering reducing agent such as ascorbic acid, reaction products which will themselves prevent the desired analysis.

This phenomenon of mercury complex interference with the reagent system can readily be determined at the laboratory branch, given the present teachings. All one need do is to incorporate the complex with the desired reagent system. That composition can then be used to measure the presence of the component in two precalibrated solutions, one containing urine having the component present, and the other the same component-containing urine, but with a relatively high amount of ascorbic acid added (about 10–100 mg/dl). The results of these analyses are then compared with results obtained from using the reagent system without the complex in the same solutions. Reasonable color concurrence between the two is indicative of acceptable noninterference of the reagent system by the mercury complex or its reduction products.

To summarize generally the above findings, both experimental and theoretical, a substantial number of ligands have been discovered which, when complexed with $Hg^{++}$, provide the solution of a problem which has for years plagued the art of analysis, in particular such analysis using dip-and-read reagent strips: incorrect or false negative readings due to the interfering effects of ascorbic acid or other similar reducing agents. These ligands arise from such seemingly unrelated generic categories as amino acids, nucleosides, secondary and tertiary amines, amides, and phosphines. Moreover, some compounds of a given category work, whereas others do not.

Given these puzzling experimental results, applicants set about finding a community of properties linking the successful ligands and complexes, but excluding those which didn't work. Four parameters appear important: (a) the ability of the ligand to covalently bind with $Hg^{++}$ to form water-soluble complexes, (b) the ability of the ligand to withstand the oxidative penchant of $Hg^{++}$ (i.e. a higher oxidation potential), (c) a $K_s$ of $10^5$ to $10^8$ or higher for the complex, and (d) the compatibility of the complex with a particular reagent system. Successful complexes satisfied all of these requirements; unsuccessful ones failed to satisfy one or more of them.

The Table below lists ligands which were experimented with (see Examples, infra), both successfully and unsuccessfully, and they are arranged accordingly. Also given in the Table are the reasons why certain ligands provide complexes with $Hg^{++}$ incapable of safeguarding a prior art glucose reagent formulation from ascorbate interference. In Table II, a designation of (1) indicates that the ligand does not bond covalently to $Hg^{++}$ or forms a water-insoluble complex, (2) indicates that the ligand lacks an oxidation potential sufficient to stave off oxidation by $Hg^{++}$, and (3) indicates complexes having too low a $K_s$.

TABLE II

| Successful Ligands | |
|---|---|
| sarcosine | uridine |
| threonine | triethanolamine |
| serine | diethanolamine |
| proline | sodium lauryolsarcosinate |

TABLE II-continued bicene [(HOCH$_2$CH$_2$)$_2$ NCH$_2$COOH]    triphenylphosphine

Unsuccessful Ligands (Reasons)

alanine (2)
glycine (2)
trishydroxymethylaminomethane (2)
glutamic acid (2)
asparagine (1 and 3)
DL-α-amino-n-butyric acid (1 and 3)
α-methylaminoisobutyric acid (1 and 3)
2,6-pyridine dicarboxylic acid (1 and 3)
Nitrilotriacetic acid (1 and 3)
Adenine (1 and 3)
Guanine (1 and 3)
Cystine (2)
Leucine (2)
m-Dimethylaminobenzoic acid (1, 2 and 3)
Amino methane sulfonic acid (1 and 3)
Sulfamic acid (1 and 3)
Glycylglycine (2)
L-Histidine (2)
Cytidine (1 and 2)
Acetone (3)
EDTA*
Morpholine (2)
Thianthrene (3)
Methyiminodiacetic acid (1)
Arginine (1 and 2)
Ornithine (1 and 2)
Lysine (1 and 2)
Citric acid*

*oxidation of interferent too slow

Although rigorous investigation as to why certain ligands did not appear effective in combating interference was not pursued in the experiments, close observation of the behavior of each of the ligands as set forth in the Examples leads pursuasively to the conclusions set forth in Table II under "(Reasons)". In addition, it is likely that relatively nonvolatile ligands will result in complexes having higher shelf life than would their more volatile counterparts.

It is appropriate at this juncture in describing the invention to attempt to provide some insight as to how complexes within the scope of the claims can be prepared. For example, mercury(II)sarcosinate can be prepared, as can many of the complexes, by adding mercuric oxide to a solution of the ligand, here sarcosine, in water. Similarly, mercuric serinate can be formed from a serine solution. These solutions can then be used as additives to standard glucose-sensitive reagents, or they can be used to isolate a purified solid form of the complex by precipitation, as with isopropanol. Of course, complexes which are prepared by other methods are within the scope of the present invention, provided they satisfy the criteria presently described and claimed.

A few words about reagent systems of the prior art used for determining the presence of test sample components should further facilitate an understanding of the presently described concepts. These reagent systems include the indicator systems described, supra, under Description of the Prior Art, and cited references there and elsewhere are hereby incorporated by reference.

One such system found especially resistant to ascorbate interference when combined with a complex presently claimed is that comprising a sugar oxidase, a peroxidatively active substance, and an oxidation-reduction indicator capable of producing a color change to H$_2$O$_2$ and the peroxidatively active substance. Depending on the particular sugar to be analyzed, an enzyme is chosen which will effect the production of H$_2$O$_2$ upon oxidation of the sugar analyte. Thus, for glucose analysis glucose oxidase is preferable. Similarly, if the analyte is to be galactose, a H$_2$O$_2$-producing enzyme is galactose oxidase.

Once H$_2$O$_2$ is formed, a peroxidatively active substance is required to facilitate activation of the particular indicator chosen. Typical peroxidatively active substances include peroxidase and hemoglobin. Among the many oxidation-reduction indicators known which produce a color change in the presence of H$_2$O$_2$ and a peroxidatively active substance are benzidine and its many chromogenic derivatives. These include o-tolidine, 2,7-diaminofluorene, 3,3',5,5'-tetra(lower alkyl)-benzidine, and the N-, N'- and N,N'-(lower alky)substituted benzidines. By the term "lower alkyl" is meant substituted and unsubstituted hydrocarbon radicals having from 1 to about 6 carbon atoms, including methyl, ethyl, n-propyl, isopropyl, cyclopropyl, n-butyl, isobutyl, tert-butyl, cyclobutyl, n-pentyl, sec-pentyl, tert-pentyl, neopentyl, cyclopentyl, n-hexyl, cyclohexyl, and all other isomers thereof.

Of course, it will be understood that there are conceivably many sugar-sensitive reagent systems which are susceptible to interference from ascorbate and similar reducing agents. It is presently believed that these systems will also benefit from the present inventive concepts, and that incorporation of applicants' complexes into such reagent systems would greatly alleviate the problem. Accordingly, such systems are contemplated as being within the scope and spirit of the present invention.

Another reagent system rendered resistant to ascorbate interference when combined with the complex of the present invention is that comprising a peroxidatively active substance and a redox indicator capable of effecting a color change in the presence of H$_2$O$_2$ and the peroxidatively active substance. Such a reagent system is known for the detection of peroxide analytes, such as cumene hydroperoxide and hydrogen peroxide.

From the reagent systems mentioned above, it is reasonable to expect that any such system based on a redox indicator having an oxidation potential significantly higher than that of ascorbic acid is suspect of being interfered with by a reducing agent having an oxidation potential similar to that of ascorbic acid. Accordingly, the present invention applies to all such reducing agent-sensitive reagent systems.

In preparing the test device of the present invention, wherein the composition is the glucose-responsive reagent described, supra, the composition comprises a glucose-responsive reagent solution in water (first solution), and a solution containing the mercury complex (second solution). The glucose-responsive solution contains a benzidine-type indicator such as 3,3',5,5'-tetramethylbenzidine, glucose oxidase, peroxidase, and buffer. A piece of filter paper is immersed and saturated with the first solution and dried. Next the dried impregnated filter paper is immersed and saturated with the second solution and dried.

In one embodiment of the invention, the paper containing the first and second solution reagents is cut into small squares, one of which is mounted at one end of a strip of polystyrene film. Adhesion of the paper to the polystyrene can be effected using a double-faced adhesive tape such as that known as Double-Stick ® marketed by 3M Co. The resultant test device can then be used to measure glucose in urine, the test being virtually uninhibited by the presence of up to 200 mg% ascorbic acid in the test sample.

The carrier matrix utilized in the presently claimed device can comprise any substance capable of being incorporated with the composition. Thus the matrix can take on many known forms such as those utilized for reagent strips for solution analysis. For example, U.S. Pat. No. 3,846,247 teaches the use of felt, porous ceramic strips, and woven or matted glass fibers. As substitutes for paper, U.S. Pat. No. 3,552,928 teaches the use of wood sticks, cloth, sponge material, and argillaceous substances. The use of synthetic resin fleeces and glass fiber felts in place of paper is suggested in British Pat. No. 1,369,139. Another British Pat. No. 1,349,623, suggests the use of a light-permeable meshwork of thin filaments as a cover for an underlying paper matrix. This reference also suggests impregnating the paper with part of a reagent system and impregnating the meshwork with other potentially incompatible reagents. French Pat. No. 2,170,397 teaches the use of carrier matrices having greater than 50% polyamide fibers therein. Another approach to carrier matrices is disclosed in U.S. Pat. No. 4,046,513 wherein the concept of printing reagents onto a suitable carrier matrix is employed. U.S. Pat. No. 4,046,514 discloses the interweaving or knitting of filaments bearing reagents in a reactant system. Preferably the carrier matrix comprises a bibulous material such as filter paper. All such carrier matrix concepts can be employed in the present invention, as can others, and all of the above-mentioned references describing same are hereby incorporated by reference into the present disclosure.

The base support member on which the impregnated carrier matrix can be mounted may take on many variations in shape, size and material of construction. Thus, it might be constructed of any substantially liquid impervious material, such as polystyrene, polyolefin, glass, paper, metal or other material. Usually, however, it is preferred that the base member of a polymeric material, such as biaxially oriented polystyrene sold by Plastic Suppliers, Inc. For most purposes it has been found preferable that the support member be relatively rigid and extend sufficiently far from the carrier matrix position to afford the user a convenient handle.

EXAMPLES

The following Examples serve to describe experiments performed in discovering and studying the present invention. They represent presently preferred embodiments, and are illustrative with respect to making and using the invention. It is to be understood, however, that they are in no way intended as limiting the scope of the invention.

A. PREPARATION OF VARIOUS COMPLEXES

Two techniques have been found experimentally to provide mercury complexes which produce the unexpected combination of stability and efficacy at eliminating reducing agents which interfere with sugar-sensitive reagent systems. These are the mercuric oxide method and the soluble salt method.

The former involves the use of HgO as a starting material, wherein the ligand and HgO are combined in distilled water to form a solution of the complex. The latter, and the technique which appears to have the broader applicability, comprises the use of such water-soluble mercuric salts as mercury(II)acetate and nitrate. Both of these techniques are illustrated by the experiments which follow.

EXAMPLE I - MERCURY(II)SARCOSINATE: THE OXIDE METHOD

Complexes of $Hg^{++}$ and amino acids can be readily formed by the addition of powdered HgO and amino acid, either sequentially or simultaneously, to water, thus forming a solution of the complex. The solution can then be used directly in the present invention, or the complex can be isolated and stored for later use. The analysis calculated for $Hg(CH_3NHCH_2COO^-)_2$ is C, 19.15; H, 3.21; N, 7.44; Hg, 53.24; O, 16.99. Found: C, 18.94; H, 3.93; N, 7.26; Hg, 53.04; O, 17.33.

When HgO is stirred with aqueous sarcosine at a 1:2 molar ratio, respectively, only two-thirds of the HgO dissolves. Use of a threefold molar excess of sarcosine effects complete dissolution. This phenomenon has not yet been satisfactorily explained, since both stoichiometries result in the same complex, i.e., $Hg(sarcosine)_2$, as is shown through elemental analysis.

In an experiment utilizing this technique, samples of HgO and sarcosine weighing 1.83 grams (g) ($8.45 \times 10^{-3}$ moles) and 3.014 g ($38.2 \times 10^{-3}$ moles), respectively, were added to ten milliliters (ml) of distilled water with stirring. An orange, opaque suspension formed which became clear after about 10-20 minutes at room temperature. The complex was isolated from this solution by precipitation utilizing isopropanol.

EXAMPLE II - MERCURY(II)SARCOSINATE: THE SALT METHOD

In the salt method for preparing mercury complexes, a mercuric salt such as the acetate or nitrate is dissolved in an appropriate solvent along with a particular ligand. Whereas amino acid complexes can be prepared with the oxide method as well as the salt method, it is the latter which finds applicability to a broad variety of ligands, many of which do not form complexes, or do so at a very slow rate, using HgO.

A sample of mercuric acetate weighing 31.0 g (0.143 moles) was dissolved in 400 ml. methanol, and 17.54 g sarcosine was dissolved in 60.0 ml. distilled water. The aqueous sarcosine was added to the methanolic solution, mixed and allowed to stand at room temperature for one hour, whereupon crystallization of mercuric sarcosinate occurred. After two hours the reaction mixture was filtered. The crystals were recovered and dried to provide 26.3 g of product (80% of theoretical yield). Refrigeration overnight of the filtrate yielded an additional 3 g of product.

EXAMPLE III - MERCURY(II)SERINATE: THE OXIDE METHOD

Mercuric serinate was prepared using the technique of Example I. Accordingly, 1.83 g HgO and 1.78 g serine were combined in 10 ml. distilled water with stirring. As in the previous experiment, a clear solution of mercury(II)serinate ultimately formed.

EXAMPLE IV - MERCURY(II)BICENATE

Reaction of HgO with bicene, bis-hydroxyethylglycine, $(HOCH_2CH_2)_2NCH_2COOH$, as in Example I, in a 1:2 molar ratio produced a clear, stable solution. No attempt to isolate the complex was made.

EXAMPLE V - MERCURY(II)PROLINATE

Reaction of HgO with proline in aqueous solution, as in Example I, at a 1:3 molar ratio produced a clear, stable solution of the Hg:proline complex.

EXAMPLE VI - MERCURY(II)THREONATE

HgO was reacted with aqueous threonine, as in Example I, at a 1:2 molar ratio to produce a clear, stable solution of the Hg:threonine complex product.

EXAMPLE VII - MERCURY(II)URIDINATE

HgO was added to an aqueous solution or uridine, as in Example I, in a 1:2 molar ratio to produce a clear, stable solution of the product Hg:uridine complex.

combined in a 1:2 molar ratio to yield a clear, stable solution. The product complex was isolated by evaporation followed by multiple acetone washings to remove sodium acetate present in the evaporation residue.

EXAMPLES XII - XXXVI

Following the procedures of Examples I or II, complexes of a great many ligands were prepared which, for the reasons listed in Table III, below, failed to satisfy the requirements of the present disclosure.

TABLE III

| Example No. | Ligand | Remarks |
|---|---|---|
| XII | Alanine | Metallic Hg formed upon aging |
| XIII | Glycine | Metallic Hg formed upon aging |
| XIV | Tris-hydroxymethylamino methane | Metallic Hg formed upon aging |
| XV | Glutamic acid | White precipitate formed which turned grey upon aging |
| XVI | Asparagine | White precipitate formed |
| XVII | DL-α-amino-n-butyric acid | White precipitate formed |
| XVIII | α-methylaminoisobutyric acid | White precipitate formed |
| XIX | 2,6-pyridine dicarboxylic acid | Orange precipitate formed |
| XX | Nitrolotriacetic acid | White precipitate formed |
| XXI | Adenine | Orange precipitate formed |
| XXII | Guanine | Orange precipitate formed |
| XXIII | Cystine | Black precipitate formed |
| XXIV | Leucine | Grey precipitate formed |
| XXV | m-Dimethylaminobenzoic acid | Brown precipitate formed |
| XXVI | Aminomethanesulfonic acid | White precipitate formed |
| XXVII | Sulfamic acid | White precipitate formed |
| XXVIII | Glycylglycine | Metallic Hg formed upon aging |
| XXIX | L-Histidine | Metallic Hg formed upon aging |
| XXX | Cytidine | White precipitate formed which greys upon aging |
| XXXI | Morpholine | Forms metallic Hg |
| XXXII | Thianthrene | No complex formation |
| XXXIII | Methyliminodiacetic acid | White precipitate formed |
| XXXIV | Arginine | Grey precipitate formed |
| XXXV | Ornithine | Brown and white precipitate formed |
| XXXVI | Lysine | Grey precipitate formed |

EXAMPLE VIII - MERCURY(II)TRIPHENYLPHOSPHINATE

A portion of triphenylphosphine (3 g) was dissolved in 50% dimethylformamide and reacted with 1.30 g HgCl$_2$ until a white precipitate formed. This complex of mercuric ion and triphenylphosphine was collected by filtration and dried. The complex dissolved in distilled water to yield a clear, stable solution.

EXAMPLE IX - MERCURY(II)DIETHANOLAMINATE

A portion of mercuric acetate weighing 2.6 g ($8.4 \times 10^{-3}$ moles) was dissolved in 10 ml. distilled water. To the solution was added 1.92 g (0.016 mole) of diethanolamine. A clear, stable solution of the complex resulted almost immediately upon addition of the ligand.

The complex was isolated by evaporation of the reaction mixture.

EXAMPLE X - MERCURY(II)TRIETHANOLAMINATE

Following the procedure of Example IX, aqueous mercuric acetate was combined with triethanolamine in a 1:2 stoichiometry. A clear, stable solution of the product Hg:triethanolamine complex resulted.

EXAMPLE XI - MERCURY(II)LAUROYLSARCOSINATE

Folloiwng the procedure of Example IX, aqueous mercuric acetate and sodium lauroylsarcosinate were

B. PREPARATION OF TEST DEVICES

In the following experiments, various complexes were formed as in Examples I-XI and combined with reagents sensitive to glucose in order to determine the effect of the complex on abating interference from ascorbic acid. The specific ligands used were sarcosine, serine, alanine, proline, bicene, and uridine.

EXAMPLE XXXVII - MERCURIC SARCOSINATE

A number of test strips were prepared using glucose-sensitive reagents and mercuric sarcosinate. Each was prepared in the form of an oblong polystyrene strip, on one end of which was mounted a square of filter paper impregnated with the composition. The paper was held in place using double-faced adhesive tape.

In preparing these test devices, a 0.2 inch wide strip of Eaton and Dikeman 204 filter paper was immersed in a first dip solution, comprising glucose oxidase, peroxidase, 3,3',5,5'-tetramethylbenzidine, and a buffer in water. The impregnated paper was then dried in an air oven at about 50° C. for about 30 minutes. Following drying, the paper was next immersed in a second dip solution comprising mercuric sarcosinate complex. After a second drying, the impregnated strip was mounted along one edge of a film of biaxially oriented polystyrene using a double-faced adhesive known as Double Stick, marketed by 3M Company. The filter paper/film composite was cut in strips perpendicular to the edge bearing the impregnated paper. The strips measured about 4×0.2 inches, the paper portion at the ends each measuring about 0.2 inches square.

The first dip solution contained the ingredients listed below. These were mixed in order as listed.

| | |
|---|---|
| 3,3',5,5'-Tetramethylbenzidine | 0.05 g |
| Acetone | 6.0 ml |
| Citrate buffer (pH 5)* | 1.88 ml |
| Tris-glutamate buffer** | 2.82 ml |
| Steol CA 460, 10% by weight in water (Stepan Chemical Co.) | 0.5 ml |
| Plasdone K-29-32 polyvinylpyrrolidone (GAF Corp.) | 6.0 ml |
| Gantrez AN-139, 10% by weight in water (GAF Corp.) | 1.5 ml |
| Ascorbic acid, 10% by weight in water | 0.05 ml |
| Glucose oxidase, 5000 I.U./ml (Miles Laboratories, Inc.) | 1.5 ml |
| Horseradish peroxidase, 68 I.U./mg (Miles Laboratories, Inc.) | 0.05 g |

*The citrate buffer solution, separately prepared, comprised 15.4 g citric acid and 68.0 g trisodium citrate in 208 ml distilled water.
**The tris-glutamate buffer solution comprised 45 g glutamic acid and 37.5 g tris-hydroxymethylaminomethane in 208 ml distilled water.

The second dip was prepared by first forming two premixes and combining them. Premix A was obtained by mixing the following ingredients in the order in which they are listed:

| | | |
|---|---|---|
| Polyvinylpyrrolidone (K-60 obtained from GAF Corp.) | 20.0 | g |
| Sodium dodecylbenzene sulfonate | 0.8 | g |
| Ninol 2012 (cocoyldiethanolamide obtained from Stepan Chemical Co.) | 1.5 | g |
| Distilled water | 124.0 | ml |

Premix B contained the complex, mercuric sarcosinate, and was prepared by mixing the following ingredients in the order as listed:

| | | |
|---|---|---|
| Distilled water | 20.0 | ml |
| Mercuric oxide | 3.66 | g |
| Sarcosine | 6.03 | g |

Premix A was added to premix B when all of the sarcosine and HgO had gone into solution.

EXAMPLES XXXVIII - XLI - TEST STRIPS UTILIZING OTHER COMPLEXES

The experiment of Example XXXVII was repeated for mercuric complexes of serine, proline, bicene and uridine, following the procedure as described. Premix A was prepared from

| | | |
|---|---|---|
| Polyvinylpyrrolidone K-60 | 10.0 | g |
| Sodium dodecylbenzene sulfonate | 0.4 | g |
| Ninol 2012 | 0.75 | g |
| Distilled water | 62.0 | ml |

Separate premix B formulations were prepared for each complex from 1.83 HgO in 10.00 ml distilled water with the following amounts of ligand.

| | | |
|---|---|---|
| Example XXXVIII | Serine | 1.79 g |
| XXXIX | Proline | 2.94 g |
| XL | Bicene | 2.77 g |
| XLI | Uridine | 4.15 g |

C. PERFORMANCE OF SEVERAL TEST DEVICES AFTER HEAT STRESSING

The test devices prepared in Examples XXXVII--XLI were stressed in order to assess stability. Accordingly, each complex was assessed by storage at room temperature for about seven days, and at three days in a 60° C. air oven. Following stressing, each set of test devices was observed to determine (a) ability to differentiate between various levels of glucose in a sample, and (b) whether the glucose analysis was subject to interference by ascorbic acid. For each set of strips bearing a different mercuric complex, samples were dipped in test solutions of pooled urine bearing glucose. The test solutions contained 0, 10, 20, 30, 40, 50, 100, 250, 500, 700 and 1,000 milligrams of glucose per deciliter of solution (mg %). The ability of a particular class of devices to determine these different glucose levels was assessed using the test strips aged at room temperature. Where color development increased with glucose concentration, a device was considered to differentiate between the concentration levels. Where no significant increase of color intensity was observed between glucose levels, differentiation was deemed equal.

In order to assess the resistance of the test devices to interference from ascorbic acid, they were tested with two sets of glucose solutions, one set at 50 mg %, the other at 100 mg %. Each set comprised three solutions which, in addition to glucose, contained 0, 100 and 200 mg % ascorbic acid, respectively. For each set of devices bearing a different mercuric complex, samples were dipped in both sets of glucose solutions. Where colors corresponding to the presence of glucose were identical regardless of ascorbate concentration a short time after dipping, the problem of interference was deemed to be solved through the presence of the mercuric complex.

EXAMPLE XLII - MERCURIC SARCOSINATE

The test devices prepared in Example XXXVII, after room temperature aging for about seven days, were tested with the various glucose solutions described above to determine ability to differentiate between glucose levels. The results, in the order of increasing color intensity, were $0 < 10 < 20 < 30 < 40 < 50 < 100 < 250 = 500 = 1000$ mg %

Devices stressed at 60° C. were substantially equally reactive.

The devices aged at room temperature were then tested in the two sets of solutions containing 50 and 100 mg % glucose, respectively. Each set comprised three solutions of varying ascorbic acid concentrations: 0, 100 and 200 mg %. In the three solutions containing 50 mg % glucose, the colors developed in the strips were substantially the same after 15 seconds. In the 100 mg % glucose solutions, the colors were nearly identical after ten seconds.

Substantially the same results were obtained with strip devices aged at 60° C. for three days.

EXAMPLE XLIII - MERCURIC SERINATE

Test devices as prepared in Example XXXVIII were stressed and tested as in Example XLII. Devices aged at room temperature yielded the following capability in differentiating between glucose levels:

0<10<20<30<40<50<100<250=500=1000 mg %

Stressed strips (60° C. for three days) had no observed decrease in response.

When observed with the ascorbic acid/glucose solutions of Example XLII, devices dipped in the 50 mg % glucose solutions required five seconds for color development to match; whereas the devices dipped in the 100 mg % solutions took ten seconds.

EXAMPLE XLIV - MERCURIC PROLINATE

Test devices prepared as in Example XXXIX were stressed and tested as in Example XLII. The devices aged at room temperature yielded the following capabilities in differentiating between glucose levels:

0<10<20<30<40<50<100<250=500=1000 mg %

Devices stressed at 60° C. for three days lost no observed decrease in activity response.

The ascorbate resistance experiment with room temperature-stressed devices showed that the three 50 mg % glucose solutions required 15 seconds to produce substantially matched color appearance in the test devices, whereas the 100 mg % glucose solutions yielded matching colors after ten seconds. The same experiment with devices aged at 60° C. for three days yielded the same results.

EXAMPLE XLV - MERCURIC BICENATE

The devices from Example XL were stressed and tested as in Example XLII. Those aged at room temperature yielded the following capabilities in differentiating between glucose levels:

0<10<20<30<40<50<100<250=500=1000 mg %

Those aged at 60° C. for three days lost no observable differentiation capability.

In the ascorbate resistance experiment, room temperature-stressed devices in the 50 mg % glucose solutions required ten seconds to produce substantially matched color appearance. Likewise, in the 100 mg % glucose solutions they yielded matching colors after ten seconds. The same experiment with devices aged at 60° C. for three days yielded the same results.

EXAMPLE XLVI - MERCURIC URIDINATE

The devices from Example XLI were stressed and tested as in Example XLII. Those aged at room temperature yielded the following capabilities in differentiating between glucose levels:

0<10<20<30<40<50<10-
0<250=500=750=1000 mg %

Those devices aged at 60° C. for three days did not respond in color at the 10 mg % level, but easily differentiated between the higher levels similarly to the devices aged at room temperature.

In the ascorbate resistance experiment, room temperature-stressed devices in the 50 mg % glucose solutions required 35 seconds to produce substantially matched color appearances, whereas in the 100 mg % glucose solutions they yielded matching colors after 60 seconds. The same experiment using strips aged at 60° C. for three days yielded similar results.

D. PRIOR ART MERCURIC COMPOUNDS

Experiments were performed to assess the performance of prior art mercuric compounds, thereby providing a basis for comparison with the present invention. U.S. Pat. No. 3,411,887 to Ku is the closest prior art known to applicants. That patent (the "Ku patent") is hereby incorporated into this disclosure by reference. It discloses three mercuric compounds for use as "trapping agents": the acetate, nitrate, and chloride (column 4, lines 9 and 10). These compounds were incorporated into test devices as shown in Example I of the Ku patent (at column 6).

EXAMPLE XLVII - MERCURIC ACETATE (KU PATENT)

In preparing this test device, two mixtures were formulated. The first contained the active ingredients for the glucose detecting reagent system, and the second contained the ingredients for the ascorbate trapping system. The detecting system contained:

| | |
|---|---|
| Ortho-tolidine dihydrochloride | 250 mg |
| Glucose oxidase | 1.9 g |
| Peroxidase | 40 mg |
| Gelatin | 1.2 g |
| F,D, and C, Soluble Red No. 3 | 60 mg |
| Buffer containing a mixture of 55.5 g anhydrous citric acid and 244.5 g trisodium citrate ground together and dissolved in 750 ml of water | 30 ml |

The following sequence was observed in preparing the detecting system. The peroxidase was dissolved in 5 ml of water and combined with a 5 ml aqueous suspension of glucose oxidase. The gelatin and F,D and C dye were dissolved in 25 ml of boiling water and cooled to room temperature. The ortho-tolidine dihydrochloride was then suspended in 12.6 ml of 2B alcohol and combined with the buffer solution. All of the above mixtures and solutions were combined in one container and thoroughly mixed. Paper strips measuring 2 inches by ¼ inch were dipped into this prepared solution and air dried at 100° C. for nine minutes.

The trapping system contained:

| | |
|---|---|
| Vinylpyrrolidone/vinyl acetate copolymer (PVV/VAE 535 - 50g % in ethanol from GAF Corp.) | 6.5 ml |
| Nonoxyl-9-phosphate (10g % in 2B alcohol - GAFAC RE 610 from GAF Corp.) | 0.7 ml |
| Dioctyl sodium sulfosuccinate (25g % in 2B alcohol - Aerosol OT from American Cyanamid Co., Industrial Chemicals & Plastics Div.) | 0.4 ml |
| Mercuric acetate | 8.0 ml |
| Sodium acetate | 2.0 g |
| Dimethylsulfoxide | 91.5 ml |

The mercuric acetate trapping agent was dissolved in dimethylsulfoxide and combined with a solution containing the thickening agent, the wetting agent and the buffer. These ingredients were then thoroughly mixed until a homogeneous solution was obtained. Approximately one-half of the impregnated strips were then coated with the homogeneous mixture comprising the trapping system by dipping the strips into the mixture.

The strips were then air dried at a temperature of 80° C. for a period of about nine minutes.

These devices were then tested in pooled urine containing concentrations of glucose ranging from 0 to 1000 mg % glucose and were found responsive over the entire concentration range. Color differentiation was possible from 10 to 250 mg % glucose.

A group of freshly prepared strips were then set aside on the laboratory bench in a tightly capped bottle containing silica gel and molecular sieves. After one week (seven days) of storage in this fashion, the devices were again tested in freshly prepared solutions of glucose in pooled urine. They gave no color response to glucose, even at a concentration of 1000 mg %. The devices had not survived room temperature, low humidity storage for one week.

EXAMPLE XLVIII - MERCURIC ACETATE (ALTERNATE PREPARATION)

Because formulations of the present invention are prepared without the dimethylsulfoxide used in the Ku patent, an experiment was conducted as in Example XLVII, above, except 91.5 ml water was used in place of the same amount of dimethylsulfoxide. It was noted while the devices were being dried that HgO began precipitating out of the mercuric acetate trapping system solution (about 15 minutes).

These devices were then tested as in Example XLVII, and responded in similar fashion both before and after storage.

EXAMPLES XLIX AND L - MERCURIC CHLORIDE AND MERCURIC NITRATE

Experiments were conducted as in Examples XLVII and XLVIII, above, except that separate sets of strips were prepared from mercuric chloride and mercuric nitrate, respectively. The amounts of these compounds used in formulating the trapping systems (and which replace the 8 grams of mercuric acetate) were 6.8 g of $HgCl_2$ and 13.4 g of $Hg(NO_3)_2$.

The devices freshly prepared from $HgCl_2$ were capable of differentiating glucose concentrations from 50 to 500 mg %. Upon aging for one week at room temperature and low humidity, they were unresponsive, even at 1000 mg % glucose. The devices prepared from $Hg(NO_3)_2$ were unresponsive, whether freshly prepared, or after storage.

E. PREPARATION AND PERFORMANCE OF A COMPOSITION CAPABLE OF DETECTING HYDROGEN PEROXIDE.

EXAMPLES LI–LXVI

A series of experiments was conducted to determine the efficacy of the present invention in rendering a peroxide-sensitive reagent system free from ascorbate interference. A reagent solution capable of forming a blue color in the presence of hydrogen peroxide, comprising a buffered solution of peroxidase and ortho-tolidine in ethanol, was prepared. Its ability to detect $H_2O_2$ in the presence of ascorbic acid and various mercuric complexes was studied.

The following ingredients were used to prepare various mercuric complexes in water, using HgO or mercuric acetate, as indicated.

| Example No. Ingredient | LI | LII | LIII | LIV | LV | LVI | LVII | LVIII | LIX | LX | LXI | LXII | LXIII | LXIV |
|---|---|---|---|---|---|---|---|---|---|---|---|---|---|---|
| | | | | | | Amount (g) | | | | | | | | |
| Mercuric Oxide | 1.83 | 1.83 | 1.83 | 1.83 | 1.83 | | | 1.83 | | 1.83 | | 1.83 | 1.83 | |
| Mercuric Acetate | | | | | | 2.69 | 2.69 | | 2.69 | | 2.69 | | | 2.69 |
| Sarcosine | 2.26 | | | | | | | | | | | | | |
| Threonine | | 3.03 | | | | | | | | | | | | |
| Serine | | | 2.67 | | | | | | | | | | | |
| Proline | | | | 2.93 | | | | | | | | | | |
| Bicene | | | | | 4.15 | | | | | | | | | |
| Triethanolamine | | | | | | 1.78 | | | | | | | | |
| Monoethanolamine | | | | | | | 1.55 | | | | | | | |
| Glutamic Acid | | | | | | | | 3.74 | | | | | | |
| Sulfamic Acid | | | | | | | | | 2.47 | | | | | |
| Ethylenediamine-tetraacetic Acid | | | | | | | | | | 2.48 | | | | |
| Glycine | | | | | | | | | | | 1.91 | | | |
| N-(2-Acetamido)iminodiacetic Acid (ADA) | | | | | | | | | | | | | 3.22 | |
| Sodium Lauroyl-sarcosinate | | | | | | | | | | | | | | 8.27 |
| Citric Acid | | | | | | | | | | | | 1.63 | | |
| Distilled Water | 10.0 | 10.0 | 10.0 | 10.0 | 10.0 | 10.0 | 10.0 | 10.0 | 10.0 | 10.0 | 10.0 | 10.0 | 10.0 | 10.0 |

It was observed that the mixtures for Examples LI–LIV and LVI were clear solutions, LV was clear with suspended crystals, LVII had a grey solid precipitate, LVIII–LXII had either white or orange precipitate present, LXIII resulted in a turbid suspension and LXIV formed a gel.

A stock solution of reagents responsive to peroxide was prepared by mixing in order the following reagents:

| | |
|---|---|
| Citrate buffer (pH 5) | 100 ml |
| Horseradish Peroxidase (70 I.U./mg) | 100 mg |
| ortho-Tolidine | 100 mg |
| Ethanol (23A) | 25 ml |

Aliquots of 1.5 ml each of this solution were added to 16 wells of a spot plate, each well having a 2.0 ml capacity. To 15 of the solution-containing wells was added 3 µl (microliters) of a 10 g/dl solution of ascorbic acid in water. The wells were labeled LI through LXVI, the ones labeled LXV and LXVI serving as control experiments without mercuric complex, and with and without ascorbic acid, respectively. Finally, a 1 µl portion of each of the mercuric complexes was added to the appropriately labeled well (LI–LXIV).

When the 16 wells were thus prepared, each was inoculated with 5 μl of a 10% solution of H₂O₂ in water, with stirring using a glass rod. After five seconds of stirring, each well was observed for the appearance of blue color. The results are tabulated as follows.

| Example No. | Ligand | Results |
|---|---|---|
| LI | Sarcosine | Blue color formed |
| LII | Threonine | Blue color formed |
| LIII | Serine | Blue color formed |
| LIV | Proline | Blue color formed |
| LV | Bicene | Blue color formed |
| LVI | Triethanolamine | Blue color formed |
| LVII | Monoethanolamine | No color |
| LVIII | Glutamic Acid | No color |
| LIX | Sulfamic Acid | No color |
| LX | Citric Acid | No color |
| LXI | Ethylenediaminetetraacetic Acid | No color |
| LXII | Glycine | No color |
| LXIII | N-(2-Acetamido)iminodiacetic acid (ADA) | Blue color formed |
| LXIV | Sodium Lauroylsarcosinate | Blue color formed |
| LXV | Control (no ascorbate) | Blue color formed |
| LXVI | Control (ascorbate present) | No color |

Examples LI–LXVI demonstrate that the complexes of the present invention are compatible with a reagent system for detecting peroxide, and that they inhibit interference with the test from ascorbic acid.

What is claimed is:

1. In a composition for determining the presence of a component in a test sample, wherein said composition comprises a reagent system containing a peroxidatively active substance, and an oxidation-reduction indicator capable of providing a detectable response in the presence of H₂O₂ and said peroxidatively active substance, and wherein said response is suceptible to being adversely influenced by the presence in said test sample of ascorbic acid, said composition further comprising a heavy metal compound which, in its ionized state, has an oxidation potential below that of said indicator, but above that of ascorbic acid, the improvement wherein said heavy metal compound is a complex of mercuric ion and one or more ligands, said ligand being covalently bound to said ion to form a water-soluble complex, and said ligand having a higher oxidation potential than said ion in its complexed state; said complex having a $K_s$ greater than about $10^7$, wherein $K_s$ is defined by the equation $$K_s = \frac{[OH^-]^2}{4 \times 10^{-26}}$$

and said complex being substantially noninterfering with respect to said reagent system.

2. The improved composition of claim 1 wherein said ligand is an amino acid, a nucleoside, a secondary amine, a tertiary amine, an amide, or a phosphine.

3. The improved composition of claim 2 wherein said ligand is sarcosine, threonine, serine, proline, bicene, uridine, triethanolamine, diethanolamine, lauroylsarcosine, urea of triphenylphosphine.

4. The improved composition of claim 1 wherein said complex is mercury (II) sarcosinate.

5. The improved composition of claim 1, 2, 3 or 4 wherein said test sample component is a sugar and wherein said reagent system comprises
an enzyme capable of promoting the oxidation of said sugar to produce peroxide,
and wherein said indicator is a chromogenic substance.

6. The improved composition of claim 5 wherein said sugar is glucose, said enzyme is glucose oxidase and said peroxidatively active substance is peroxidase.

7. The improved composition of claim 5 wherein said chromogenic substance is benzidine, o-tolidine, 3,3',5,5'-tetra(lower alkyl)benzidine, N-, or N,N'-poly(lower alkyl)-substituted benzidine, 2,7-diaminofluorene or mixtures thereof.

8. The improved composition of claim 6 wherein said chromogenic substance is benzidine, o-tolidine, 3,3',5,5'-tetra(lower alkyl)benzidine, N-, or N,N'-poly(lower alkyl)-substituted benzidine, 2,7-diaminofluorene or mixtures thereof.

9. A test device for determining the presence of a component in a test sample, said device comprising a carrier matrix incorporated with the improved composition of claim 1, 2, 3 or 4.

10. A test device for determining the presence of a component in a test sample, said device comprising a carrier matrix incorporated with the improved composition of claim 5.

11. A test device for determining the presence of a component in a test sample, said device comprising a carrier matrix incorporated with the improved composition of claim 6.

12. A test device for determining the presence of a component in a test sample, said device comprising a carrier matrix incorporated with the improved composition of claim 7.

13. A test device for determining the presence of a component in a test sample, said device comprising a carrier matrix incorporated with the improved composition of claim 8.

14. A method for determining the presence of a component in a test sample, said method comprising contacting said sample with the improved composition of claim 1, 2, 3 or 4, and observing any detectable response.

15. A method for determining the presence of a sugar in a test sample, said method comprising contacting said sample with the improved composition of claim 5, and observing any detectable response.

16. A method for determining the presence of a sugar in a test sample, said method comprising contacting said sample with the improved composition of claim 6, and observing any detectable response.

17. A method for determining the presence of a sugar in a test sample, said method comprising contacting said sample with the improved composition of claim 7, and observing any detectable response.

18. A method for determining the presence of a sugar in a test sample, said method comprising contacting said sample with the improved composition of claim 8, and observing any detectable response.

* * * * *